US005433745A

United States Patent [19]
Graham et al.

[11] Patent Number: 5,433,745
[45] Date of Patent: Jul. 18, 1995

[54] CORNEAL IMPLANTS AND METHODS FOR PRODUCING SAME

[75] Inventors: Richard S. Graham, Irvine; Crystal M. Cunanan, Mission Viejo; James E. Francese, Anaheim, all of Calif.

[73] Assignee: Allergan, Inc., Irvine, Calif.

[21] Appl. No.: 135,875

[22] Filed: Oct. 13, 1993

[51] Int. Cl.⁶ .................................................. A61F 2/16
[52] U.S. Cl. ................... 623/5; 351/160 H; 523/105; 523/114
[58] Field of Search .............. 623/5, 6; 351/160 H; 427/2.24; 523/105, 114

[56] References Cited

U.S. PATENT DOCUMENTS

| | | | |
|---|---|---|---|
| 3,885,078 | 5/1975 | Wichterle et al. | 351/160 H |
| 4,388,428 | 6/1983 | Kuzma et al. | 351/160 H |
| 4,589,964 | 5/1986 | Mayhan et al. | |
| 4,693,939 | 9/1987 | Ofstead | 623/5 X |
| 4,806,382 | 2/1989 | Goldberg et al. | 623/5 X |
| 4,845,132 | 7/1989 | Masuoka et al. | |
| 4,851,003 | 7/1989 | Lindstrom | 427/2.24 X |
| 4,919,659 | 4/1990 | Horbett et al. | |
| 4,961,954 | 10/1990 | Goldberg et al. | 427/2 |
| 4,983,181 | 1/1991 | Civerchia | 623/5 |
| 5,007,928 | 4/1991 | Okamura et al. | 427/2.24 X |
| 5,108,428 | 4/1992 | Capecchi et al. | 623/5 |
| 5,171,318 | 12/1992 | Gibson et al. | 623/5 |
| 5,192,316 | 3/1993 | Ting | 623/5 |

OTHER PUBLICATIONS

Hino et al, A Study on Collagen-Plastic Composites as Biomaterials, "Biocompatibility of Tissue Analogs", vol. II, pp. 71–87.

Suzuki et al, Graft Copolymerization of Acrylamide onto a Polyethylene Surface Pretreated with a Glow Discharge, Macromolecules 1986, 1804–1808.

Yeh et al, Blood compatibility of surfaces modified by plasma polymerization, Journal of Biomedical Materials Research, vol. 22, 795–818 (1988).

Petit et al, Quanitation of Rabbit Corneal Epithelial Cell Outgrowth on Polymeric Substrates in Vitro, "Investigative Ophthalmology & Visual Science", vol. 31, No. 11, Nov. 1990.

Horbett et al, Hydrophilic-Hydrophobic Copolymers as Cell Substrates: Effect on 3T3 Cell Growth Rates, Journal of Colloid and Interface Science, vol. 104, No. 1, Mar. 1985.

Dreyfuss et al, Graft Copolymers, vol. 7, pp. 551–579 "Encyclopedia of Polymer Science and Engineering".

Gombotz et al, Gas-Discharge Techniques for Biomaterial Modification, vol. 4, Issue 1 (1987) pp. 1–42, "Critical Reviews in Biocompatibility".

Lydon et al, Cellular interactions with synthetic polymer surfaces in culture, Biomaterials 1985, vol. 6 Nov., pp. 396–402.

Kaplan et al, Medical Polymers and Plasma Technology, Technical Notes, Plasma Science, Foster City, California pp. 1–5.

On The Surface, vol. II, No. I, Improved Biocompatibility by Surface Modification, Metro-Line Industries, Inc. Corona, California.

Special Report, Using Gas Plasma to Reengineer Surfaces, Nancy B. Mateo, Reprinted from Medical Product Manufacturing News, Sep./Oct. 1990 pp. 1–2.

Dekker et al, Adhesion of endothelial cells and adsorption of serum proteins on gas plasma-treated polytetrafluoroethylene, Biomaterials 1991, vol. 12 Mar., pp. 130–138.

H. Boenig, Plasma Polymerization, vol. 11, pp. 249–261, Academic Press, Inc., Orlando, Fla. 1986 "Encyclopedia of Polymer Science and Engineering".

Ratner et al, Plasma Deposition and Treatment for Biomaterial Applications, "Plasma Deposition of Polymer Films", Academic Press, Boston 1989.

*Primary Examiner*—Mary Beth O. Jones
*Attorney, Agent, or Firm*—Frank J. Uxa, Jr.; Gordon L. Peterson

[57] ABSTRACT

New corneal implants and methods for producing such implants are disclosed. The present corneal implants comprise a lens body which is optically clear and is structured to be surgically attached in or on the cornea of a mammalian eye, the lens body including a core having an outer surface and made of a hydrogel composition containing water and a hydrophilic polymeric material, and a coating comprising a synthetic polymeric component located on the outer surface, covalently bonded to the hydrogel composition and having enhanced ability to support epithelial cell growth and/or adhesion relative to the hydrogel composition.

21 Claims, 1 Drawing Sheet

CORNEAL IMPLANTS AND METHODS FOR PRODUCING SAME

BACKGROUND OF THE INVENTION

The present invention relates to corneal implants and methods for producing such implants. In particular, the invention relates to corneal implants structured to be surgically attached in or on the cornea of a mammalian eye which include a hydrogel composition and which have enhanced ability to support epithelial cell growth and/or adhesion relative to the hydrogel composition.

The cornea comprises five layers, including an outer layer of epithelial cells, Bowman's membrane immediately posterior of the cells, the stroma immediately posterior of Bowman's membrane, Descemet's membrane immediately posterior of the stroma and the endothelium immediately posterior of Descemet's membrane. A number of surgical operations involve implanting a corrective lens structure into or onto one or more of these corneal components. For example, in one form of eye surgery, the layer of epithelial cells is removed and a corrective lens structure is placed and secured at the location where the cells were removed. In another form of eye surgery, the layer of epithelial cells is removed and then a wedge-shaped annulus from Bowman's membrane and the underlying stroma is removed. An incision is then made from the posterior end of the resulting groove radially outwardly in an annular zone to define a flap. A corrective lens structure is attached by inserting the wing of the lens structure beneath the corneal flap and fixing, e.g., suturing, it in place. In addition, a corrective lens structure can be placed entirely within the stroma. This surgical procedure involves making an incision in the cornea to gain access to the stroma and also involves disrupting the stroma by placing a lens structure therein.

In each of these surgical procedures, it is highly desirable, even necessary, for the long term viability of such lens onlays or implants that the cornea, e.g., the epithelial cells and/or stromal keratocytes, grow onto the lens structure and/or adhere to the lens structure. Achieving such growth and adhesion has been one substantial problem inhibiting the use of such corneal onlay and implant procedures.

Hydrogel compositions have been suggested for use as materials of construction for corneal implants. As used herein, the term "hydrogel composition" refers to a polymeric composition including a sufficient amount of water to cause the composition to swell relative to the anhydrous polymeric material. Such hydrogel compositions often include at least about 38% by weight of water, and may include as much as 60% or 80% or more by weight of water. One concern of using hydrogel compositions as corneal implants is the relative inability of such compositions to support the growth and/or adhesion of epithelial cells on and/or to the implants. However, hydrogel compositions have other desired properties, such as optical clarity, durability, and relative inertness which make such compositions very attractive as corneal implant materials of construction. It would be advantageous to provide corneal implants made of compositions including hydrogels which have an enhanced ability to support the growth and/or adhesion of epithelial cells on and/or to the implants.

SUMMARY OF THE INVENTION

New corneal implants and methods for producing such implants have been discovered. The present invention takes advantage of the attractive properties of hydrogel compositions as corneal implant materials of construction while, at the same time, providing corneal implants which more effectively support the growth and/or adhesion of epithelial cells on and/or to the implants. The present modifications, as described hereinafter, render lens structures which comprise hydrogel compositions with the ability to support the growth of corneal epithelial, thus making such lens structures useful as synthetic epikeratophakia lenses.

In one broad aspect of the present invention, corneal implants are provided which comprise a lens body which is optically clear and is structured to be surgically attached in or on the cornea of a mammalian eye. This lens body includes a core having an outer surface and made of a hydrogel composition containing water and a hydrophilic polymeric material. A coating, preferably comprising a polymeric material and more preferably a synthetic polymeric material, is located on the outer surface and is covalently bonded to the hydrogel composition. This coating has enhanced ability to support at least one, preferably both, of epithelial cell growth and epithelial cell adhesion relative to the hydrogel composition. Preferably, the polymeric material which comprises the coating has increased hydrophobicity relative to the hydrophilic polymeric material.

The use of relatively hydrophobic polymers to coat the hydrogel composition core of the present corneal implants result in a relatively hydrophobic surface which is capable of supporting corneal epithelial cell growth, for example, as well as tissue culture polystyrene. The coating, for example, the hydrophobic coating, is preferably sufficiently thin and/or otherwise compatible with the swelling of the hydrogel composition so that no surface cracking or hazing is apparent. The final coating should be optically clear, nutrient permeable, stable and adherent to the underlying hydrogel.

In one particularly useful embodiment, the present corneal implants involve lens bodies which further comprises a cytophilic component located on the coating and being present in an amount effective to enhance the initial cytophilicity of the lens body relative to an identical lens body without the cytophilic component. More preferably, the cytophilic component comprises a collagen-containing component.

In another broad aspect of the present invention, methods for producing corneal implants in the form of lens bodies which are optically clear and are structured to be surgically implanted in or on the cornea of a mammalian eye. Such methods comprise providing a hydrophilic polymeric component which when hydrated forms a hydrogel composition in the form of a core of such a lens body; and forming a coating on the hydrophilic polymeric component, which coating is preferably hydrophobic relative to the hydrophilic polymeric component, is covalently bonded to the hydrophilic polymeric component and has enhanced ability to support epithelial cell growth and/or adhesion relative to the hydrogel composition. In one embodiment, the forming step includes contacting the hydrophilic polymeric component with a coating precursor to form a precursor coated hydrophilic polymeric component; and subjecting this precursor coated hydrophilic polymeric component to conditions effective to produce the coating on the hydrophilic polymeric component. In a particularly useful embodiment, the forming step comprises polymerizing a coating precursor in the presence of a plasma effective to at least facilitate the polymerization and form a polymer; and depositing the polymer on the hydrophilic polymeric component.

These and other aspects and other advantages of the present invention are set forth in the following detailed description and claims, particularly when considered in conjunction with the accompanying drawings in which like parts bear like reference numerals.

DETAILED DESCRIPTION OF THE INVENTION

Figure 1:
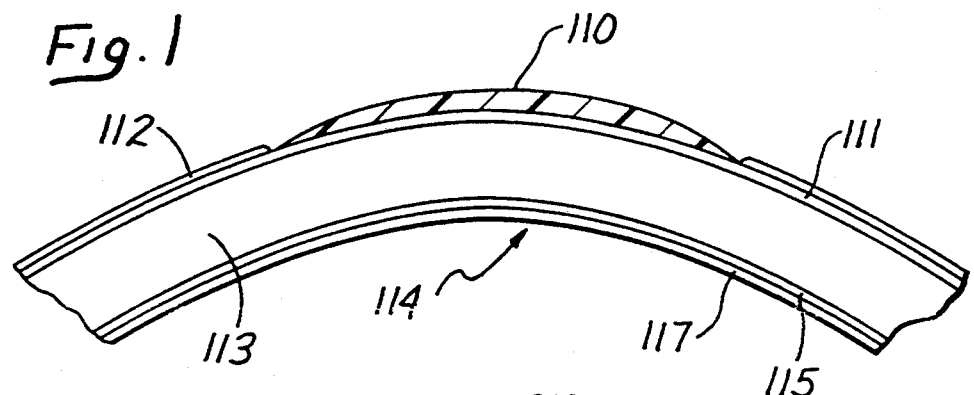
FIG. 1 is an enlarged axial, cross-sectional view showing an ocular device according to the present invention attached to a cornea.

The present invention relates to corneal implants which comprise a lens body that is optically clear and is structured to be surgically attached in or on the cornea of a mammalian eye. Such lens bodies include a core having an outer surface and made of a hydrogel composition containing water and a hydrophilic polymeric material.

Any suitable hydrophilic polymeric material may be employed in the present invention. Examples of hydrophilic polymeric materials are those which may be used in producing contact lenses. Specific examples of useful hydrophilic polymeric materials include polymers derived in whole or in part from monomers which possess an unsaturated vinyl or allyl group, undergo ordinary radical polymerization, and produce polymers which exhibit hydrophilicity. Such monomers include, but are not limited to, acryl type monomers, methacryl type monomers, unsaturated amide type monomers, diene type monomers, and triene type monomers which meet the requirements mentioned above. Typical examples of such monomers include (meth)acrylamides, N-methyl(meth)acrylamides, N,N-dimethyl(meth)acrylamides, N,N-methylethyl(meth)acrylamides, N,N-diethyl(meth)acrylamides, (meth)acrylic acids, 2-hydroxyethyl(meth)acrylates, N, N-dimethylaminoethyl (meth)acrylates, N,N-diethylaminoethyl(meth)acrylates, N-vinylpyrrolidone, p-styrene sulfonic acid, vinyl sulfonic acid, 2-methacryloyloxyethyl sulfonic acid, 3-methacryloyl oxy-2-hydroxy propyl sulfonic acid, allyl sulfonic acid, methacryl sulfonic acid, 2-acrylamide-2-methylpropane sulfonic acid, and the like and mixtures thereof.

The hydrophilic monomers can often be used either alone (to produce homopolymers) or in combination with one or more other monomers (to produce copolymers). The hydrophilic polymeric component may partially incorporate therein one or more hydrophobic monomers to the extent that the incorporated monomers do not jeopardize the desired hydrophilicity of the resulting polymeric component. The present hydrogel compositions preferably has a water content of at least about 50%, more preferably at least about 60% or even at least about 70%, by weight.

A coating, preferably comprising a polymeric material and more preferably comprising a synthetic polymeric material, is located on the outer surface of the hydrogel composition and is covalently bonded to the hydrogel composition. This coating has enhanced ability to support epithelial cell growth and/or adhesion relative to the hydrogel composition. Preferably, the polymeric material which comprises the coating has increased hydrophobicity relative to the hydrophilic polymeric material of the hydrogel composition.

Any suitable coating may be employed in the present corneal implants provided that such coating and the resulting corneal implant function as described herein. Examples of the coating precursors from which the present coatings can be prepared include compounds which are classical monomers (including one or more functional groups) used to produce synthetic polymeric materials, and normally non-functional compounds which are capable of being modified or otherwise activated, for example, at the conditions at which the coating is formed, to become reactable or polymerizable to form and/or be included in the coating. Among the classical monomers which may be employed are, for example, olefins, such as ethylene, propylene, styrene, diphenylethylene and the like; substituted olefins, such as partially chlorinated and/or fluorinated olefins (as noted above) and the like; amides, such as acrylamide, N-methylacrylamide, N,N-dimethylacrylamide and the like; acrylates and methacrylates, such as benzyl acrylate, phenoxyethyl acrylate, acetoacetoxyethyl methacrylate, N-(3-aminopropyl) methacrylates and the like; unsaturated silicon-containing monomers, such as vinyl diphenylethoxysilane and the like; other unsaturated monomers, such as vinyl benzyl chloride and the like; substituted counterparts thereof and mixtures thereof. Examples of useful non-functional compounds include paraffins, such as methane, ethane, substituted counterparts thereof and mixtures thereof; other relatively low molecular weight hydrocarbons, preferably having a molecular weight of less than about 200 and more preferably less than about 100, and substituted counterparts thereof and mixtures thereof; other organic compounds, such as alcohols, ethers, esters, amines, carboxylic acids, aldehydes, ketones (for example, acetone, benzophenone and the like) and substituted counterparts thereof and mixtures thereof.

As used herein, the term "substituted counterparts thereof" refers to such compound in which one or more hydrogen atoms are replaced by one or more other species including, but not limited to, monovalent hydrocarbon groups, such as alkyl, alkenyl (such as ethenyl, propenyl, butenyl and the like unsaturated hydrocarbon groups having 2 to about 20 or more carbon atoms) and aryl; heterocyclic groups; halogen such as F, Cl, Br and I; $NH_2$; $NO_2$; OH; alkoxy; alkylthio; aryloxy; arylthio; alkanoyl; alkanoyloxy; aroyl; aroyloxy; acido; amido; alkylamino; dialkylamino; arylamino; alkylarylamine; diarylamino; alkanoylamino; alkylsulfinyl; alkylsulfenyt; alkylsufonyl; alkylsulfonylamido; azo; benzyl; carboxy; cyano; guanyl; guanidino; imino; phosphinyl; phosphorus; silyl; thioxo; ureido or vinylidene or where one or more carbon atoms are replaced by one or more other species including, but not limited to, O or S.

The present coating precursors can be employed alone or can be employed together with one or more other coating precursors.

The coating on the hydrogel composition is preferably sufficiently thin so as to remain substantially free of cracks. This is important so as to preserve the optical clarity of the present corneal implants. A particularly useful embodiment provides that the coating be less than about 0.3 micron, more preferably less than about 0.1 micron, thick. This coating on the hydrogel composition provides an optically clear, glucose permeable, stable coating that greatly enhances the cytophilicity and protein binding ability of the hydrogel composition.

In a preferred embodiment, the coated hydrogel composition can be further modified to improve its initial cytophilicity by including an additional coating of a cytophilic component, for example, on its surface. Any suitable cytophilic component may be employed in this additional coating providing that the cyclophilic component and the resulting corneal implant function as described herein. Among the cytophilic components useful in the present invention are various growth factors and adhesion factors which promote the growth and adhesion, respectively, of the corneal cells, as described herein. In one embodiment, the cytophilic component is one or more proteins, peptides (meaning to include therein peptides, polypeptides and the like) and mixtures thereof. Useful cytophilic components include those selected from the group consisting of fibronectin, collagen, collagen composites, other collagen-containing components, cell attachment protein, anti-gelatin factor, cold-insoluble globulin, chondronectin, laminin, epidermal growth factor (EGF), mussel adhesive protein, derivatives of each of the above and mixtures thereof. Collagen-containing components, meaning to include collagen, collagen composites and other collagen-containing components, and mixtures thereof are especially useful.

The present corneal implants can be made using conventional techniques modified as described herein. In particular, the hydrogel composition core of the corneal implant can be produced in accordance with conventional techniques, for example, employing a mold in which one or more monomers making up the hydrophilic polymeric composition are polymerized. Alternately, the lens can be machined from an already formed hydrophilic polymeric composition to form the desired hydrogel composition core.

After the core is formed, the core and/or the core including the polymeric coating is subjected to one or more techniques, such as plasma grafting, gamma radiation grafting, chemical methods (such as the use of multi-functional derivatives, as discussed herein) and/or heat treatment methods, to produce the coating or the additional coating of cytophilic component on the core.

In a particularly useful embodiment, the hydrogel composition core is subjected to a plasma in the presence of one or more polymeric components or precursors of polymeric components at conditions effective to form the coating, preferably a hydrophobic polymeric coating, on the surface of the core.

This plasma can be a radio frequency, inductively-coupled plasma produced in a plasma chamber by charging the chamber with the component or components from which the coating is derived, preferably at a sub-atmospheric pressure of about 0.01 torr mm Hg or greater, more preferably, at a pressure in the range of about 0.05 torr to about 0.3 torr. The preferred output power is in the range of about 10 watts to about 500 watts, more preferably about 15 watts to about 120 watts and still more preferably about 20 watts to about 90 watts.

This plasma treating occurs for a sufficient time to provide the desired coating onto the core. Such time preferably is in the range of about 1 minute to about 60 minutes or more, more preferably about 5 minutes to about 60 minutes. The specific components included in the plasma exposing step, the exposure time, power and/or other parameters may be varied depending upon the equipment and the particular core and other materials involved, and can be readily optimized based upon the disclosure herein using routine experimentation.

The use of gamma radiation to effect the covalent bonding of a coating onto the surface of the core can be accomplished by subjecting the core to gamma radiation at conditions effective for such purpose. The gamma radiation is preferably provided in the presence of the component or components from which the coating is derived so as to activate such components to form the polymeric coating onto the core.

Chemical methods can be employed and involve functionalizing, if necessary, the component or components from which the polymeric coating is derived. Such functionalizing is effective so that a chemical reaction can take place between the hydrophilic polymeric component making up the core and the component or components from which the coating is to be derived. Examples of producing reactable groups onto an otherwise unreactable component are described herein with regard to the cytophilic component. Similar derivatives can be produced from components to produce the coating, for example, the hydrophobic polymeric coating. Also, functional or reactable precursors can be employed and reacted with the hydrophilic polymeric component making up the core using conventional procedures well known in the art.

In order to covalently bond the cytophilic component onto the implant, it may be necessary to derivatize either one or more of the cytophilic component, the component making up the coating and the hydrophilic polymeric component included in the implant. The derivative or derivatives employed depend, for example, on the specific materials used in the implant. In one particularly useful embodiment, one of the component making up the coating or the cytophilic component is reacted with a difunctional component. One of the functional groups of the difunctional component reacts with, and is covalently bonded to, the component making up the coating or the cytophilic component and the other functional group is available to be covalently bonded to the other of the component making up the coating or the cytophilic component.

Any suitable difunctional component may be employed provided that it has the ability to covalently bond to both the specific hydrophilic polymeric component and/or the component making up the coating and the cytophilic component being used. Of course, the difunctional component should have no substantial adverse effect on the implant or on its use. Examples of difunctional components which may be employed with certain cytophilic components include aldehydes, such as glutaraldehyde and the like, and imides, such as carbodiimide and the like.

The difunctional component may be reacted with the hydrophilic polymeric component and/or the component making up the coating and the cytophilic component in separate reaction steps or in a single reaction step with all reactants present.

In another embodiment, the covalent bonding of the hydrophilic polymeric component and/or the component making up the coating and the cytophilic component may be promoted or induced by exposing these components to radiation, e.g., gamma radiation, or to a plasma treatment. A hydrogel composition modified to include the coating or the combination of the coating and an additional coating of a cytophilic component provides a corneal implant on which corneel epithelial cells grow and to which such cells adhere.

Heat treating the coated core can be advantageously used to more securely adhere the coating or coatings to the core. Heat treatment can be used in combination with plasma grafting, gamma radiation and chemical methods to produce very useful coated corneal implants. The heat treatment should be such as to not cause any substantial detrimental effect to the core or to the coating or coatings on the core.

Referring now to FIG. 1, an ocular device in the form of a corneal onlay, shown generally at 110, is situated on and attached (sutured) to the Bowman's membrane 111 of a living cornea 114. Corneal onlay 110 is made in accordance with and has the chemical make-up and properties of the lens of Example 17. Also included in cornea 114 is epithelial cell layer 112, stroma 113, Descemet's membrane 115 and the endothelium 117. Corneel onlay 110, which is structured to correct one or more vision problems caused by defects in cornea 114 or in one or more other components of the eye, is set in place by surgically stripping or abrading away a desired area of the epithelial cell layer 112, placing corneal onlay 110 on this stripped area and securing corneal onlay 110 in place by suturing it to Bowman's membrane 111. The onlay 110 is placed with respect to the cornea 114 as shown in FIG. 1, so that the corneal onlay 110 is coaxial with the optical axis of the eye.

Once this surgical procedure is accomplished, epithelial cell layer 112 grows onto and attaches or adheres to corneal onlay 110.

Figure 2:
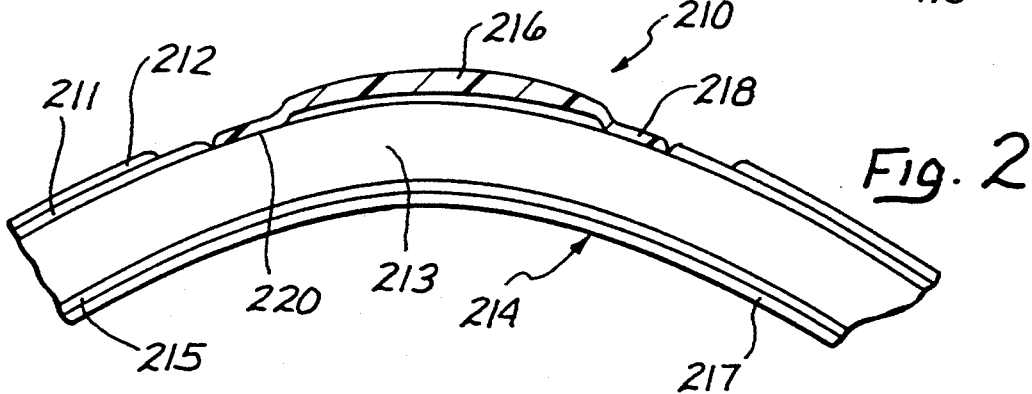
FIG. 2 is an enlarged axial, cross-sectional view showing another ocular device according to the present invention attached to a cornea.

Referring now to FIG. 2, an ocular device in the form of an alternate corneal onlay or epikeratophakia lenticula, shown generally at 210, is situated on and attached (sutured) to the Bowman's membrane 211 of a living cornea 214. Each element of cornea 214 in FIG. 2 which is also shown as an element of cornea 114 in FIG. 1 has a reference numeral increased by 100 relative to the same element shown in FIG. 1.

Corneal onlay 210 is made of substantially the same material as is corneal onlay 110. Corneal onlay 210 comprises a circular optic 216 and an annular wing 218 surrounding the optic. The onlay 210 is placed with respect to the cornea 214 as shown in FIG. 2, with the optic 216 being coaxial with the optical axis of the eye and with the annular wing 218 being received in an annular abraded zone 220. This zone 220 is obtained by stripping and/or abrading a portion of the epithelial cell layer 212 and the Bowman's membrane 211. A useful apparatus and procedure for performing this stripping/abrading are described in commonly assigned U.S. Pat. No. 4,834,148, filed Sep. 29, 1987, which is incorporated in its entirely herein by reference.

Corneal onlay 210, and in particular optic 216, is structured to correct one or more problems caused by defects in cornea 214 or in one or more other components of the eye.

Once the surgical procedure of securing corneal onlay 210 in place as shown in FIG. 2 is accomplished, epithelial cell layer 212 grows onto corneal onlay 210 and attaches or adheres to corneal onlay 210.

Corneal onlay 210 is made of substantially the same material as is corneal onlay 110.

Figure 3:
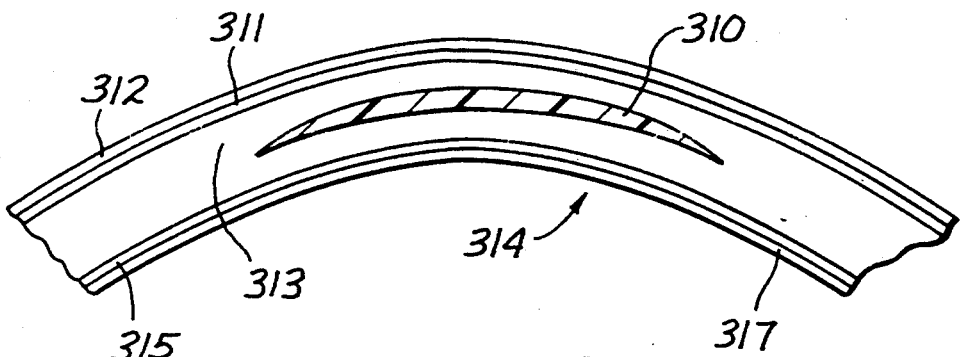
FIG. 3 is an enlarged axial, cross-sectional view showing an ocular device according to the present invention inserted in the stroma of a cornea.

Referring now to FIG. 3, an ocular device in the form of an intrastromal lens, shown generally at 310, is situated in the stroma 313 of living cornea 314. Each element of cornea 314 in FIG. 3 which is also shown as an element of cornea 114 in FIG. 1 has a reference numeral increased by 200 relative to the same element shown in FIG. 1.

Lens 310 is made of substantially the same material as the corneal onlay 110. The lens 310 is coaxial with the optical axis of the eye and is placed and secured in the stroma 313 using conventional surgical procedures. Lens 310 is structured to correct one or more vision problems caused by defects in cornea 314 or in one or more other components of the eye.

After lens 310 is surgically implanted in stroma 313 as shown in FIG. 3, the lens 310 becomes adhered to the tissue of the stroma. Ultimately, the stroma 313 is securely attached to lens 310.

The following non-limiting examples illustrate certain features of the present invention.

EXAMPLES 1 TO 13

Dry epikeratophakia lenses made of a hydrophilic polymeric component were provided for testing. The hydrophilic polymeric component employed was a crosslinked copolymer containing 70% by weight vinyl pyrrolidinone, 30% by weight methyl methacrylate, less than 0.1% by weight of allyl methacrylate and a minor effective amount, less than 0.1% by weight of a crosslinking agent, ethyleneglycol dimethacrylate. This hydrophilic polymeric component, which forms a hydrogel including about 70% by weight of water, is commercially available, being sold by Allergan, Inc. under the trademark Lidofilicon A.

Each of a series of these dry lenses was placed in a commercially available plasma chamber and the chamber was evacuated to approximately 0.8 torr. Argon gas was metered into the plasma chamber at the rate of about 1.0 ml/min. After the system had stabilized, the plasma power (13.56 MHz radio frequency) was set to 30 watts and the plasma was ignited for 5 minutes. This plasma, which can be considered an etching plasma, cleaned and activated the exterior surface of the lenses.

The lenses were removed from the plasma unit and the optical side of each of the lenses was treated with 5 microliters of a given monomer. The excess monomer was blotted off with a paper towel to produce a very thin film of monomer on the surface of the lens. This monomer film was covalently bonded to the hydrophilic polymeric material by exposing the lens to a second argon plasma. The monomer coated lens was placed in the plasma unit and the chamber was evacuated to 0.8 torr with an argon flow rate of 0.5 ml/min. The plasma power was set to 30 watts and the plasma was ignited for 1 minute to graft polymerize the coating to the lens. This polymer coating was more hydrophobic (less hydrophilic) than the based hydrophilic polymeric material. The plasma unit was returned to ambient pressure and the lens was removed, washed with water (three times with 20 ml of water) and tested for epithelial cell migration, optical transparency, appearance of surface cracks and glucose diffusivity.

Selected results of these tests are shown in Table 1:

TABLE 1

| LENS | COATING DERIVED FROM | CELL MIGRATION VALUE |
|---|---|---|
| Control A[1] | No coating | <0.25 |
| Control B[2] | No coating | <0.25 |
| 1 | styrene | 0.61 |
| 2 | vinyl benzyl chloride | 0.80 |
| 3 | benzyl acrylate (BZA) | 0.52 |
| 4 | vinyl diphenylethoxysilate | 0.52 |
| 5 | diphenylethylene | 0.30 |
| 6 | phenoxyethyl acrylate (PEA) | 0.89 |
| 7 | PEA | 0.76 |
| 8 | BZA | 0.93 |
| 9 | Benzophenone | 0.36 |
| 10 | PEA | 1.01 |
| 11 | acetoacetoxyethyl methacrylate | 0.14 |
| 12 | N-(3-aminopropyl) methacrylate | 0.23 |
| 13 | PEA | 0.73 |

[1]Lens tested with no coating or plasma treating.
[2]Lens tested after plasma etching with no coating.

As shown in Table 1, the modified lenses had cell migration values ranging from 0.14 to 1.06, and except for Lenses 11 and 12, all had cell migration values of 0.30 and above. The cell migration value is one important measure of the cell growth and adhesion on the material. The higher the cell migration value the higher the protein adsorption affinity and the greater the ability of a material to support cell, for example, epithelial cell, growth. Untreated lenses, that is Control A and Control B (as well as other commercially available hydrogel compositions used in contact lenses), had cell migration values of less than 0.25 and, thus, do not support cell growth at all.

Each of the present modified lenses, upon hydration, was optically clear, and suffered substantially no interference with the hydration or expansion of the hydrogel. The glucose diffusivity of each hydrated lens remained substantially unchanged as a result of the modification.

EXAMPLE 14 TO 16

A dry lens, as described in Examples 1 to 16, was subjected to an activating plasma at an argon pressure of 0.1 torr, an argon flow rate of 5 ml/min. and a power level of 25 watts for 5 minutes. Styrene vapor was allowed into the plasma chamber (styrene flow and pressure being equal to 0.5 ml/min. and 0.01 torr) and the plasma was ignited. The gas phase polymerization of the styrene vapor deposits (precipitates) a thin film of polymer derived from styrene onto the activated surface of the hydrophilic polymeric component. The resulting bonding of this polymer precipitate to the substrate surface is believed to have occurred at many different sites, resulting in a very stable film. The modified lens made in accordance with this procedure had a cell migration value of 0.88 and a glucose diffusivity of $1.3 \times 10^{-6}$ cm$^2$/sec. This experiment was repeated two times.

Selected results from these tests are shown in Table 2.

TABLE 2

| LENS | COATING DERIVED FROM | CELL MIGRATION FACTOR |
|---|---|---|
| 14 | Styrene | 0.88 |
| 15 | Styrene | 0.94 |
| 16 | Styrene | 1.06 |

Further, each of these modified lenses, upon hydration, was optically clear and suffered substantially no interference with the hydration or expansion of the hydrogel. The cell migration values of these lenses are shown in Table 1 as Lenses 14, 15 and 16.

A variety of plasma reaction conditions can be used to deposit and bond the coatings on and to graft and polymerize the monomers or other organic materials to the hydrophilic polymeric materials. Chemical methods, electron beam, methods and gamma grafting methods can also be used, although these methods are not as amenable as plasma grafting techniques to modify the surface of an optical lens. Although the cell migration values of the modified lenses were substantially enhanced over the original hydrophilic polymeric material, the cell migration value can be further enhanced by applying, for example, by adsorbing and/or plasma grafting and the like techniques, an additional coating of a cytophilic component, such as collagen or one or more other growth-promoting proteins, on the first coating.

EXAMPLES 17 TO 44

A number of modified hydrophilic polymeric material lenses (base material as described in Examples 1 to 16) were further modified as follows.

10 microliters of a commercially available collagen material (or other cytophilic component as shown in Table 3) was applied to the modified lens and allowed to dry for two to three hours. The dry lens was then placed in a plasma chamber, and the chamber evacuated to 0.8 torr with an argon flow rate of 0.5 ml/min. The plasma was ignited for 1 minute to graft the surface adsorbed collagen (or other cytophilic component) to the underlying modified hydrophilic polymeric material. The adsorption of collagen, air drying and plasma grafting steps could, if desired, be repeated one or more times to build a thicker and more uniform coating of cytophilic component. This coating step may also involve other biomolecules, for example, fibronectin, laminin, etc., which could be used alone or incorporated into the collagen coating to promote cell growth or stabilize the collagen coating to proteolytic digestion.

Lenses further modified in accordance with the method described above had very good cell migration values, for example, on the order of about 1.5 and above. The plasma grafted cytophilic component was firmly attached and reasonably stable to hydrolysis. For example, one sample including plasma grafted collagen was hydrolyzed for two weeks at 37° C. in water and the cell migration fell only slightly from 2.1 to 1.7. In comparison, a similar hydrolysis of a sample where the collagen was just physically adsorbed resulted in reducing the cell migration value to 0.8.

In another test, a thin layer of collagen composite gel containing 5% by weight collagen, 10% by weight of methyl methacrylate, and 85% water, was compressed onto a modified lens in a polypropylene contact lens mold and then gamma grafted. The dimensions of the gamma grafted composite layer were controlled by the cavity dimensions of the polypropylene contact lens molds and the lens. Samples made from this method had very good cell migration values, on the order of 2.0 to about 2.4, which is consistent with the high cell migration values observed with collagen composites in the past. The collagen composite layer was optically clear, cytophilic and reasonably well attached to the modified lens. The adhesion of the collagen composite to the lens was strong enough to withstand the surgical procedure and allow the lens to be implanted in the eye.

Table 3 summarizes the cell migration values of further modified lenses.

TABLE 3

| LENS | COATING DERIVED FROM | ADDITIONAL COATING | CELL MIGRATION VALUE |
|---|---|---|---|
| 17 | Styrene | Collagen[1] | 1.74, 2.48 |
| 18 | PEA | Collagen[1] | 3.10, 1.83 |
| 19 | Styrene | Collagen[1] | 1.94, 2.38 |
| 20 | PEA | Collagen[1] | 2.10, 1.80 |
| 21 | PEA | Collagen[1] | 2.12 |
| 22 | — | Gelatin | 0.79 |
| 23 | — | Heparan Sulfate | 0.0 |
| 24 | — | Heparin | 0.13 |
| 25 | — | Fibronectin | 0.66 |
| 26 | PEA | Collagen[1] | 2.62 |
| 27 | PEA | Collagen[1] | 2.39 |
| 28 | PEA | Collagen Composite[2] | 2.02, 2.38 |
| 29 | PEA | Collagen[1] | 1.95 |
| 30 | Lens 29 with glutaraldehyde post treatment | | 1.61 |
| 31 | Lens 29 with EDC[3] post-treatment | | 1.38 |
| 32 | Lens 29 with ultraviolet light post-treatment | | 1.43 |
| 33 | PEA | Collagen Composite[2] | 1.50, 2.48 |
| 34 | Styrene | Collagen Composite[2] | 2.09 |
| 35 | Styrene | Collagen[1] | 1.93, 2.04 |
| 36 | PEA | Collagen[1] | 1.61, 1.67 |
| 37 | Lens 36 with glutaraldehyde post-treatment | | 1.30 |
| 38 | PEA | Collagen[1] | 1.30 |
| 39 | Lens 38 with glutaraldehyde post-treatment | | 1.54, 1.63 |
| 40 | Lens 38 with heat treatment | | 1.90 |
| 41 | PEA | Collagen[1] | 1.82 |
| 42 | Lens 41 with glutaraldehyde post-treatment | | 1.41 |
| 43 | Lens 41 with UCARLNK[4] post-treatment | | 1.46 |
| 44 | Lens 41 with heat treatment | | 1.17 |

[1] A commercial collagen product sold by Celtrix Laboratories under the trademark Vitrogen C1.
[2] A collagen composite gel containing 5% by weight of collagen 10% by weight of methyl methacrylate and 85% by weight water.
[3] EDC is 1-Ethyl-3-(3-dimethylaminopropyl) carbodimide.
[4] UCARLNK ® is a trademark for a multi-functional carbodimide sold by Union Carbide.

Placing the cytophilic component directly on the hydrophilic polymeric component results in only relatively minor, if any, cell migration value enhancement. See Lenses 22 to 25. Each of these further modified lenses, upon hydration, was optically clear and suffered substantially no interference with the hydration or expansion of the hydrogel.

EXAMPLE 45

Lenses with either a thin layer of collagen or collagen composites on top of the modified hydrophilic polymeric component lenses (such as Lenses 19 and 34 were successfully implanted into rabbits and partially reepithelized within one to two weeks. The surface modification techniques described above produced a surface coating on a hydrogel lens which allowed corneal epithelial cells to grow and adhere to the surface coating, making such lens useful as a synthetic epikerathophakia lens.

While this invention has been described with respect to various specific examples and embodiments, it is to be understood that the invention is not limited thereto and that it can be variously practiced within the scope of the following claims.

What is claimed is:

1. A corneal implant comprising a lens body which is optically clear and is structured to be surgically attached in or on the cornea of a mammalian eye, said lens body including a core having an outer surface and made of a hydrogel composition containing water and a hydrophilic polymeric material, and a coating comprising a synthetic polymeric component located on said outer surface, covalently bonded to said hydrogel composition and having enhanced ability to support at least one of epithelial cell growth and epithelial cell adhesion relative to said hydrogel composition, said synthetic polymeric material has increased hydrophobicity relative to said hydrophilic polymeric material.

2. The corneal implant of claim 1 wherein said hydrogel composition includes at least about 60% by weight of water.

3. The corneal implant of claim 1 wherein said coating is sufficiently thin so as to remain substantially free of cracks.

4. The corneal implant of claim 1 wherein said coating is less than about 0.3 micron thick.

5. The corneal implant of claim 1 wherein said lens body further comprises a cytophilic component located on said coating and being present in an amount effective to enhance the initial cytophilicity of said lens body relative to an identical lens body without said cytophilic component.

6. The corneal implant of claim 5 wherein said cytophilic component comprises a collagen-containing component.

7. The corneal implant of claim 5 wherein said cytophilic component is covalently bonded to at least one of said hydrogel composition and said coating.

8. The corneal implant of claim 1 wherein said lens body is structured to be surgically attached on the cornea of a mammalian eye.

9. A corneal implant comprising a lens body which is optically clear and is structured to be surgically attached in or on the cornea of a mammalian eye, said lens body including a core having an outer surface and made of a hydrogel composition containing water and a hydrophilic polymeric material, a coating located on said outer surface, covalently bonded to said hydrogel composition and having enhanced ability to support at least one of epithelial cell growth and epithelial cell adhesion relative to said hydrogel composition, and a cytophilic component located on said coating and being present in an amount effective to enhance the initial cytophilicity of said lens body relative to an identical lens body without said cytophilic component.

10. The corneal implant of claim 9 wherein said cytophilic component comprises a collagen-containing component.

11. The corneal implant of claim 9 wherein said cytophilic component is covalently bonded to at least one of said hydrogel composition and said coating.

12. A composition useful as a corneal implant comprising a core having an outer surface and made of a hydrogel composition containing water and a hydrophilic polymeric component and a coating comprising a synthetic polymeric material located on said outer surface, covalently bonded to said hydrogel composition and having enhanced ability to support at least one of epithelial cell growth and epithelial cell adhesion relative to said hydrogel composition, said synthetic polymeric material having increased hydrophobicity relative to said hydrophilic polymeric material.

13. The composition of claim 12 wherein said hydrogel composition includes at least about 60% by weight of water, and said coating is less than about 0.3 micron thick.

14. The composition of claim 12 which further comprises a cytophilic component located on said coating and being present in an amount effective to enhance the initial cytophilicity of said composition relative to an identical composition without said cytophilic component.

15. A corneal implant comprising a lens body which is optically clear and is structured to be surgically attached in or on the cornea of a mammalian eye, said lens body including a core having an outer surface and made of a hydrogel composition containing water and a hydrophilic polymeric material, and a coating less than about 0.3 micron thick which comprises a synthetic polymeric component located on said outer surface, covalently bonded to said hydrogel composition and having enhanced ability to support at least one of epithelial cell growth and epithelial cell adhesion relative to said hydrogel composition.

16. The corneal implant of claim 15 wherein said hydrogel composition includes at least about 60% by weight of water.

17. The corneal implant of claim 15 wherein said coating is sufficiently thin so as to remain substantially free of cracks.

18. The corneal implant of claim 15 wherein said lens body further comprises a cytophilic component located on said coating and being present in an amount effective to enhance the initial cytophilicity of said lens body relative to an identical lens body without said cytophilic component.

19. The corneal implant of claim 18 wherein said cytophilic component comprises a collagen-containing component.

20. The corneal implant of claim 18 wherein said cytophilic component is covalently bonded to at least one of said hydrogel composition and said coating.

21. The corneal implant of claim 15 wherein said lens body is structured to be surgically attached on the cornea of a mammalian eye.

* * * * *